US007122333B2

(12) United States Patent
Iwata et al.

(10) Patent No.: US 7,122,333 B2
(45) Date of Patent: Oct. 17, 2006

(54) METHOD AND REAGENT FOR VISUALLY MEASURING ATP

(75) Inventors: Ken Iwata, Uji (JP); Tadao Suzuki, Uji (JP)

(73) Assignee: Unitika Ltd., Hyogo (JP)

( * ) Notice: Subject to any disclaimer, the term of this patent is extended or adjusted under 35 U.S.C. 154(b) by 263 days.

(21) Appl. No.: 10/476,649

(22) PCT Filed: Nov. 19, 2002

(86) PCT No.: PCT/JP02/12071

§ 371 (c)(1),
(2), (4) Date: Nov. 4, 2003

(87) PCT Pub. No.: WO03/044222

PCT Pub. Date: May 30, 2003

(65) Prior Publication Data

US 2004/0142401 A1 Jul. 22, 2004

(30) Foreign Application Priority Data

Nov. 21, 2001 (JP) ............................ 2001-356141

(51) Int. Cl.
*C12Q 1/48* (2006.01)

(52) U.S. Cl. .......................................... 435/15; 435/26

(58) Field of Classification Search .................. 435/15, 435/26

See application file for complete search history.

(56) References Cited

U.S. PATENT DOCUMENTS

| | | | | |
|---|---|---|---|---|
| 4,629,697 A | * | 12/1986 | Limbach et al. | 435/26 |
| 4,806,415 A | * | 2/1989 | Fossati | 435/14 |
| 4,882,276 A | * | 11/1989 | Imahori et al. | 435/89 |
| 4,923,796 A | | 5/1990 | Deneke et al. | |
| 5,905,029 A | | 5/1999 | Andreotti et al. | |
| 5,912,139 A | * | 6/1999 | Iwata et al. | 435/26 |
| 5,916,761 A | * | 6/1999 | Koga et al. | 435/21 |
| 6,043,047 A | | 3/2000 | Foote et al. | |

FOREIGN PATENT DOCUMENTS

| | | | |
|---|---|---|---|
| EP | 0 071 087 | A1 | 2/1983 |
| EP | 821069 | A | 1/1998 |
| EP | 924302 | A | 6/1999 |
| JP | 59-166099 | A | 9/1984 |
| JP | 62-239054 | A | 10/1987 |
| JP | 63-11848 | A | 1/1988 |
| JP | 64-23900 | A | 1/1989 |
| JP | 4-7000 | B2 | 11/1992 |
| JP | 4-360700 | A | 12/1992 |
| JP | 6-129988 | A | 5/1994 |
| JP | 2001-252095 | A | 9/2001 |

OTHER PUBLICATIONS

Chittock et al. (1991) Biochem. Soc. Trans. 19, 160S.*

Abeles RH, Frey PA, Jencks WP "Biochemistry" Jones and Bartlett Pub., Boston, MA (1992) pp. iii, 239, 240, 244, 259.*

Koshland DE (1952) JACS 74, 2286-2292. "Effects of Catalysts on the Hydrolysis of Acetyl Phosphate."*

Stocchi, et al., Simultaneous Extraction and Reverse-Phase High-Performance Liquid Chromatographic Determination of Adenine and Pyridine Nucleotides in Human Red Blood Cells; Analytical Biochemistry 146, 118-124 (1985).

Ramos-Salazar, et al., Fluorometric Determination of Adenine Nucleotides and Adenosine by Ion-Paired, Reverse-Phase, High-Performance Liquid Chromatography; Analytical Biochemistry 145, 9-13 (1985).

XP-002302324—Wolfgang Berke et al., "Continuous Regeneration of ATP in Enzyme Membrane Reactor for Enzymatic Syntheses", Biotechnology and Bioengineering (1988), vol. 32, No. 2, pp. 130-139.

Supplementary European Search Report dated Nov. 8, 2004.

* cited by examiner

*Primary Examiner*—Ralph Gitomer
(74) *Attorney, Agent, or Firm*—Sughrue Mion, PLLC

(57) ABSTRACT

The object of the invention is to provide a handy type visually determinable ATP measuring reagent which can be easily handled and has good measuring sensitivity. The invention is an ATP measuring reagent which rendered possible visual determination by amplifying the reaction to form glucose 6-phosphate from glucose through the joint use of ATP contained in a sample and acetyl phosphate contained in the reagent with glucokinase and acetate kinase contained in the reagent, and further leading it to a visualizable color reaction by the combination of glucose-6-phosphate dehydrogenase and diaphorase.

17 Claims, 4 Drawing Sheets

METHOD AND REAGENT FOR VISUALLY MEASURING ATP

This application is filed under Rule 371 based on PCT/JP02/12071 filed Nov. 19, 2002 which claims priority to Japan application 2001-356141 filed Nov. 21, 2001.

TECHNICAL FIELD

This invention relates to a method and a reagent for the measurement of ATP, more particularly to a handy type, visually determinable ATP measuring method and measuring reagent, providing for easy determination, good handling ability, and good measuring sensitivity.

BACKGROUND OF THE INVENTION

Since ATP is a high energy compound and concerned in the energy metabolism of many biological bodies, measurement of ATP is used as an index for biological activity. Illustratively, measurement of ATP is used in various indexes such as viable cell count, metabolic changes in cells, control of food quality including ripeness and putridity of food, water quality check in the water quality purification and the like.

As a method for measuring ATP, a method of a high performance liquid chromatography using a reverse phase column has been described in *Analytical Biochemistry*, vol. 146, p. 118, 1985, *Analytical Biochemistry*, vol. 145, p. 9, 1985, and the like.

Examples of known methods for measuring ATP making use of enzyme reactions include a bioluminescence method in which a light generated by the reaction of firefly luciferase with its luminescence substrate luciferin in the presence of ATP is measured using a luminometer or the like (U.S. Pat. No. 5,905,029, JP-A-6-129988 and the like), a method in which the reaction is amplified by jointly using hexokinase and pyruvate kinase and ATP is finally measured by chemiluminescence using isoluminol (JP-A-64-23900 and the like), and a method in which nucleoside phosphorylase and xanthine oxidase are added to a solution containing an ATP-related compound, and hydrogen peroxide formed by the reaction is determined (JP-A-63-11848 and the like).

In addition, as a method for the enzymatic measurement of ADP as a degraded product of ATP, a method is known in which ADP is converted into ATP by the action of a kinase in the presence of a phosphate compound, the dephosphorylation compound formed by this reaction from the phosphate compound is oxidized by the action of a dehydrogenase in the presence of NAD, and NADH formed by this reaction is measured by the action of diaphorase (U.S. Pat. No. 4,923,796 and the like).

Also, examples of known measuring methods of ATP by a color reaction having a possibility of carrying out visual determination include a method in which an ATP degrading enzyme is allowed to act upon ATP, and molybdenum blue formed by the reaction of the thus formed phosphoric acid with molybdenum is measured (JP-A-4-360700 and the like), a method in which nicotinamide mononucleotide and adenylyl transferase are reacted in a solution containing ATP, and the thus formed NAD is determined by carrying out a coenzyme cycling reaction which uses reduction type NAD as the coenzyme with a oxidation reduction reaction system which uses NAD as the coenzyme (JP-A-59-166099 and the like), and a method in which an amplification reaction of ATP is carried out using AMP, glucose 6-phosphate, adenylate kinase and glucokinase, and the thus formed glucose is led to a color reaction (U.S. Pat. No. 6,043,047 and the like).

Separately from this, a case is known in which multiple coloration was realized in order to increase accuracy of visual determination in the color reaction using diaphorase and the like, by simultaneously using two or more tetrazolium compounds as the chromogen (Japanese Patent No. 1,782,359, JP-A-62-239054 and the like). However, nicotinamide adenine dinucleotide itself or glucose is considered as the substance to be measured, and only 1 molecule of the chromogen is changed to a pigment based on 1 molecule of the substance to be measured. Because of this, a measurable concentration range of the substance to be measured is limited to the concentration of the substance to be measured in the assay reagent solution. Since a concentration range of the substance to be measured is limited naturally by the assay reagents, it is not suited for practical use.

Regarding the method which uses a high performance liquid chromatography or a luminometer, it is basically a measuring method which uses a measuring apparatus, and the measuring apparatus is expensive in the actual field, so that concern has been directed towards a visually determinable ATP measuring reagent which does not require a measuring apparatus and has an easy determination handling ability.

Also, in the molybdenum blue-measuring method among the measuring methods of ATP by a color reaction having a possibility of carrying out visual determination, ATP is not directly measured but phosphoric acid formed by degrading ATP is measured. Because of this, it is highly possible to measure phosphoric acid and the like which are not related to the ATP derived from living bodies and the like. Phosphoric acid is also contained frequently in various synthetic products.

Also, in the determination method by carrying out a coenzyme cycling reaction which uses reduction type NAD as the coenzyme with a oxidation reduction reaction system which uses NAD as the coenzyme, ATP added to a system in which NAD is not present is converted into NAD, and its amplification is carried out by the cycling reaction of NAD and reduced type NAD. In this case, since the sample to be measured is mainly originated from organisms, contamination of NAD and reduced type NAD contained in the sample cannot be avoided, and contamination of NAD and reduced type NAD contained in the sample become large noises by causing a cycling reaction, so that a possibility of causing a large hindrance to the measurement of ATP is very high. Thus, when various possible noises are taken into consideration, it is considered that measurement of ATP by directly incorporating it in the reaction is necessary.

The method in which ATP is directly incorporated into the reaction by carrying out an amplification reaction of ATP using AMP, glucose 6-phosphate, adenylate kinase and glucokinase uses a reverse direction dephosphorylation reaction of glucose from glucose 6-phosphate, which is not the direction of the original catalytic reaction of glucokinase. This reverse reaction is small in comparison with the normal reaction. Since it is known that the reaction of ADP into ATP is hardly generated, it is expected that the amount of glucokinase used becomes great in carrying out this reaction system. Since it is generally known that glucokinase or the like enzyme which reacts with ATP is contaminated with very little amount of ATP, particularly when measurement of a trace amount of ATP is the object as in the the present invention, it can be easily considered that the contaminating ATP, though in an extremely small amount, will exert great influence on the measurement.

The invention contemplates providing an ATP measuring method and reagent, which can perform visual determination without requiring a high performance liquid chromatography, luminometer or similar expensive measuring apparatus and also can show good sensitivity by directly incorporating ATP and measuring ATP by making use of the normal reaction of glucokinase.

BRIEF SUMMARY OF THE INVENTION

For the purpose of solving the aforementioned problems, the present inventors have carried out intensive studies and found as a result of the efforts that a visualizable color reaction can be effected by the combination of a coupled enzyme reaction system comprising two enzymes acetate kinase and either of glucokinase or hexokinase with another coupled enzyme reaction system comprising two enzymes, i.e., glucose-6-phosphate dehydrogenase and diaphorase, thereby accomplishing the invention.

That is, the first invention resides in a visually determinable ATP measuring method, characterized in that glucose 6-phosphate is formed in response to the amount of ATP in a sample by the action of a coupled enzyme reaction system comprising two enzymes acetate kinase and either of glucokinase or hexokinase in the presence of acetyl phosphate and glucose. A pigment is subsequently formed in response to the amount of formed glucose 6-phosphate by the action of another coupled enzyme reaction system comprising two enzymes glucose-6-phosphate dehydrogenase and diaphorase or an electron carrier, or one enzyme and one electron carrier, in the presence of nicotinamide adenine dinucleotide (NAD) or nicotinamide adenine dinucleotide phosphate (NADP) and a chromogen, and then the amount of ATP in the sample is measured by determining the thus formed pigment.

The second invention resides in a visually determinable ATP measuring reagent, characterized in that it comprises a reagent which comprises acetyl phosphate and glucose and two coupled enzymes acetate kinase and glucokinase or hexokinase and forms glucose 6-phosphate in response to the amount of ATP in a sample, and another reagent that comprises nicotinamide adenine dinucleotide (NAD) or nicotinamide adenine dinucleotide phosphate (NADP) and a chromogen and two coupled enzymes glucose-6-phosphate dehydrogenase and diaphorase or an electron carrier, or one enzyme and one electron carrier, and forms a pigment in response to the amount of glucose 6-phosphate.

For further effecting the above first invention and second invention, the third invention resides in a visually determinable ATP measuring method which rendered possible conversion of the color development originated from ATP in the reagent into multiple colors by the simultaneous use of two or more tetrazolium compounds as chromogens in the aforementioned reaction system, and in a visually determinable ATP measuring reagent which contains two or more chromogens.

For further effecting the above first invention, second invention and third invention, the fourth invention resides in a visually determinable ATP measuring method which is provided with a function to obtain the same determination result at any time during a period of the reaction until determination, for example from 5 minutes to 2 hours, through the coexistence of a reaction terminator in a reagent containing the aforementioned reaction system thereby effecting termination of the coupled reactions described in the first invention and the second invention after a predetermined period of time, whereas it is necessary to carry out the determination after a constant period of time by the measuring methods described in the first invention, the second invention and the third invention, and in a visually determinable ATP measuring reagent in which a reaction terminator is allowed to coexist in the reagent.

Figure 1:
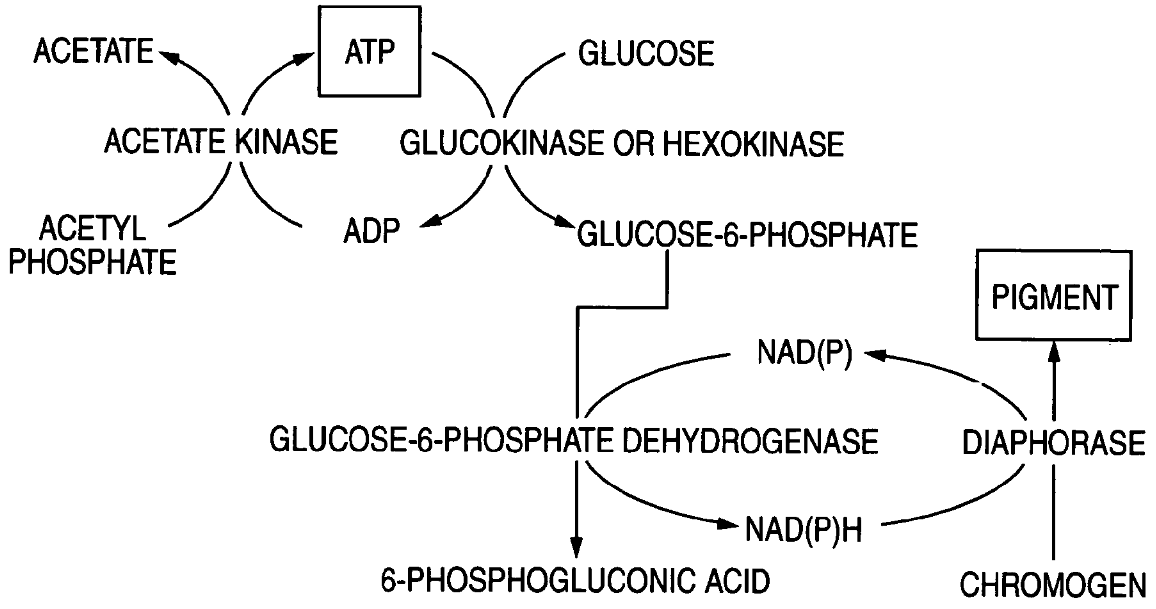
FIG. 1 is an illustration showing reaction principle of the measuring method of the invention.

In this connection, abbreviations in the drawings have the following meanings. ATP: adenosine triphosphate, ADP: adenosine diphosphate, NAD(P): nicotinamide adenine dinucleotide or nicotinamide adenine dinucleotide phosphate, NAD(P)H: reduced type nicotinamide adenine dinucleotide or reduced type nicotinamide adenine dinucleotide phosphate

DETAILED DESCRIPTION OF THE INVENTION

The color reaction to be used in the invention is based on the combination of coupled enzyme reaction systems in which the following two cycling reactions shown in FIG. 1 are generated.

First, ATP contained in a sample is changed to ADP by forming glucose 6-phosphate through phosphorylation of glucose by the action of glucokinase in the reagent. Further, the ADP thus formed from ATP is regenerated into ATP by the action of acetate kinase in the presence of acetyl phosphate. In this manner, when ATP or ADP as a degraded product of ATP is added even in a trace amount to a system in which glucose, glucokinase, acetyl phosphate and acetate kinase coexist, glucose 6-phosphate is continuously formed at a rate depending on the amount of added ATP or ADP until glucose or acetyl phosphate is completely consumed.

Next, the thus formed glucose 6-phosphate is converted into gluconate 6-phosphate by the oxidation reaction of glucose-6-phosphate dehydrogenase in the coexistence of nicotinamide adenine dinucleotide (to be referred to as NAD hereinafter) or nicotinamide adenine dinucleotide phosphate (to be referred to as NADP hereinafter), and NAD or NADP is reduced into reduced type nicotinamide adenine dinucleotide (to be referred to as NADH hereinafter) or reduced type nicotinamide adenine dinucleotide phosphate (to be referred to as NADPH hereinafter). The thus formed NADH or NADPH reduces a chromogen to cause coloration by the action of diaphorase and is regenerated into NAD or NADP. In this manner, the formed glucose 6-phosphate produces a pigment and induces coloration by a system in which NAD or NADP, glucose-6-phosphate dehydrogenase, chromogen and diaphorase coexist.

Thus, according to the reaction principle to be used in the invention, a cycling reaction is generated by the addition of ATP to a system in which glucose, glucokinase, acetyl phosphate and acetate kinase coexist, thereby forming glucose 6-phosphate at a rate in response to the amount of added ATP, and then the thus formed glucose 6-phosphate produces a pigment and induces coloration when supplied to a cycling reaction system in which NAD or NADP, glucose-6-phosphate dehydrogenase, chromogen and diaphorase coexist.

Since this coloration rate is dependent upon the amount of added ATP after all, the added ATP can be measured quantitatively by observing this coloration by a predetermined period of time. In addition, being a color reaction, visual determination can also be carried out.

In this connection, as a reaction system analogous to this reaction principle, those which aim at determining glucose are known (JP-A-10-33196, JP-A-11-253193). In such methods, glucose is measured using a color reaction by a reaction system containing ATP, NADP and tetrazolium and hexokinase, glucose-6-phosphate dehydrogenase and diaphorase. In case that glucose and ATP in this system are simply replaced with each other, the coloration can be barely observed when ATP is present in an amount of from micromol to millimol equivalent. Since the ATP to be measured by the invention is an extremely trace amount of ATP to be used as various indexes such as viable cell count, metabolic changes in cells, control of food quality including ripeness and putridity of food, water quality check in the water quality purification and the like, the expected measuring method requires such a sensitivity that at least 1 nanomol as the amount of ATP can be sufficiently measured. Since this is only an amount of 1/1,000 or less of the amount necessary for carrying out the reaction, which can be deduced from Michaelis constant Km and the like parameters of the enzymes to be used, it is considered that at least 1,000 times or more amplification of ATP is necessary for inducing coloration.

In addition, methods for forming glucose 6-phosphate from glucose by regenerating ATP by cycling reaction using a bioreactor are described in "Enzyme in Carbohydrate Synthesis", chapter 9, pp. 111–120, 1991 (republication of ACS Symposium Series No. 466, US Society of Chemistry), *Denpun Kagaku-shi* (Journal of Starch Science), vol. 33, p. 218, 1986, and the like. However, these methods are an amplification reaction of ATP at a level of from millimol amount to mol amount and are absolutely different from the nanomol level amplification of the present invention. Also, regarding the cycling of ATP, about 100 times of cycling is carried out spending several hours, which is completely different from the present invention in which 1,000 times or more of amplification is expected within several minutes.

In using the measuring method of the present invention, it may be any condition with the proviso that coloring of the pigment can be determined through simultaneous progress of the aforementioned two cycling reactions. For example, a buffer solution containing acetyl phosphate, glucose, NAD or NADP, acetate kinase, glucokinase (or hexokinase), glucose-6-phosphate dehydrogenase, diaphorase and a chromogen may be prepared. By adding dropwise an ATP-containing sample to this buffer solution and observing the coloration, ATP in the sample can be measured. Regarding kind and concentration of the buffer solution, there are no particular limitations unless they inhibit the reaction.

Also, preferably, it is desirable that acetyl phosphate, glucose, NAD or NADH, acetate kinase, glucokinase (or hexokinase), glucose-6-phosphate dehydrogenase, diaphorase, a chromogen and ATP are present in the same solution at the same time at the time of the reaction, and their conditions are not particularly limited until the reaction and they may be in a liquid state, a powder state, a state impregnated into a test paper, nonwoven fabric or the like, or even a state dried on a test paper or nonwoven fabric, each independently, at the same time or as a combination of two or more.

In addition, being a nature of the invention, living body samples are frequently used. For example, glucose, NAD, various enzymes and the like are frequently contained in living body samples at relatively high concentrations, so that it is possible to all appearances to construct a measuring reagent which does not contain such components. However, since the essence of the invention is that all of the components are present at the time of the measurement of ATP, it is of no importance whether each of these components is artificially added or originated from samples.

According to the invention, a salt form of NAD or NADP is not particularly limited with the proviso that it can effect the reaction.

According to the invention, being a nature of the reaction, NADH or NADPH may be used instead of NAD or NADP. The NADH or NADPH is converted into NAD or NADP through the oxidation by chromogen and diaphorase which are composing elements of the second cycling system. Thus, the same results are obtained when NADH or NADPH is used instead of NAD or NADP. In that case, the chromogen is also reduced and develops color, and this becomes an early stage coloration which corresponds to a blank of the reagent. However, since increase in the blank is not desirable in the practical use, it is desirable to use NAD or NADP. In addition, according to the invention, contamination of NAD with its degradation product ADP is observed in some cases, so that it is more desirable to use NADP in practical use.

The amount of NAD or NADP or the like used is not particularly limited with the proviso that it is within a range for sufficiently effecting the reaction, but when cost, production and the like are taken into consideration, the range of its practical using amount is from 0.1 nanomol to 1,000 micromol, more preferably from 1 nanomol to 100 micromol, based on 1 ml of the reaction solution at the time of the reaction.

Regarding the acetate kinase [EC 2.7.2.1] to be used in the invention, organisms and the like as its supply source are not particularly limited, and those derived from *Bacillus stearothermophilus, Escherichia coli* and the like microorganisms can be exemplified. Among them, the acetate kinase derived from *Bacillus stearothermophilus* is particularly desirable due to its storage stability.

The amount of acetate kinase used is not particularly limited with the proviso that it is within a range for sufficiently effecting the reaction, but when cost, production and the like are taken into consideration, the range of its practical using amount is from 0.001 to 10,000 units, more preferably from 0.01 to 1,000 units, most suitably from 0.1 to 500 units, based on 1 ml of the reaction solution at the time of the reaction.

Regarding the glucokinase [EC 2.7.2.2] or hexokinase [EC 2.7.1.1] to be used in the invention, organisms and the like as its supply source are not particularly limited, and those derived from *Bacillus stearothermophilus, Zymomonas mobilis*, yeast and the like microorganisms can be exemplified.

Also, regarding the difference between glucokinase and hexokinase, properties of respective enzymes such as reaction with glucose, specificity of the reaction and the like are slightly different, but the essence of the reaction of both enzymes is the same in terms that they form ADP by converting glucose into glucose 6-phosphate in the presence of ATP, so that no difference can be found between both enzymes from the viewpoint of the reaction in using in the invention. However, being excellent in storage stability, glucokinase derived from *Bacillus stearothermophilus* or *Zymomonas mobilis* is particularly desirable.

The amount of glucokinase or hexokinase used is not particularly limited with the proviso that it is within a range for sufficiently effecting the reaction, but when cost, production and the like are taken into consideration, the range of its practical using amount is from 0.001 to 10,000 units, more preferably from 0.01 to 1,000 units, most suitably from 0.1 to 500 units, based on 1 ml of the reaction solution at the time of the reaction.

Regarding the glucose-6-phosphate dehydrogenase [EC 1.1.1.49] to be used in the invention, organisms and the like as its supply source are not particularly limited, and those derived from *Bacillus stearothermophilus, Zymomonas mobilis, Leuconostoc mesenteroides*, yeast and the like microorganisms can be exemplified. Among them, microbial enzyme is desirable because of good productivity and easy obtainment, and being excellent in storage stability, glucose-6-phosphate dehydrogenase derived from *Bacillus stearothermophilus, Zymomonas mobilis* or *Leuconostoc mesenteroides* is particularly desirable.

The amount of glucose-6-phosphate dehydrogenase used is not particularly limited with the proviso that it is within a range for sufficiently effecting the reaction, but when cost, production and the like are taken into consideration, the range of its practical using amount is from 0.001 to 10,000 units, more preferably from 0.01 to 1,000 units, most suitably from 0.1 to 50 units, based on 1 ml of the reaction solution at the time of the reaction.

In addition, in order to accelerate reaction of glucose-6-phosphate dehydrogenase, 6-phosphogluconolactonase [EC 3.1.1.31] may be added. This enzyme is an enzyme which catalyzes hydrolysis of 6-phosphogluconolactone into 6-phosphogluconic acid during the process in which 6-phosphogluconolactone is formed from glucose 6-phosphate oxidized by glucose-6-phosphate dehydrogenase, and 6-phosphogluconic acid is formed from this 6-phosphogluconolactone by its spontaneous hydrolysis. By the addition of this, a more efficient reaction becomes possible.

In addition to this, in order to further increase the reaction sensitivity, 6-phosphogluconate dehydrogenase [EC 1.1.1.41] may be added. This 6-phosphogluconate dehydrogenase enzyme oxidizes 6-phosphogluconic acid into ribulose 5-phosphate in the presence of NAD or NADP and thereby forms NADH or NADPH. In the pigment-forming cycling system after formation of glucose 6-phosphate in the invention, formation of NADH or NADPH necessary for reducing the chromogen becomes 2 molecules based on 1 molecule of glucose 6-phosphate by the addition of this enzyme, so that the cycling efficiency increases about 2 times and, further, a high sensitivity measurement of ATP becomes possible.

The amounts of 6-phosphogluconolactonase and 6-phosphogluconate dehydrogenase used are not particularly limited with the proviso that they are within a range for sufficiently effecting the reaction, but when cost, production and the like are taken into consideration, the range of their practical using amount is respectively from 0.001 to 10,000 units, more preferably from 0.01 to 1,000 units, most suitably from 0.01 to 50 units, based on 1 ml of the reaction solution at the time of the reaction.

Regarding the diaphorase to be used in the invention, organisms and the like as its supply source are not particularly limited with the proviso that it can catalyze the reducing reaction of a chromogen in the coexistence of nicotinamide adenine dinucleotide (or nicotinamide adenine dinucleotide phosphate), and those which are derived from *Bacillus stearothermophilus, Clostridium kluyveri* and the like microorganisms and derived from swine heart can be exemplified. Among them, microbial enzyme is desirable because of good productivity and easy obtainment, and being excellent in storage stability, diaphorase I [EC 1.6.4.3] or diaphorase II [EC 1.6.99.-] derived from *Bacillus stearothermophilus* is particularly desirable.

In addition, it is generally known that the same effect can be obtained when phenazine methosulfate (PMS), Meldola's Blue or the like electron carrier is used instead of diaphorase.

The amount of diaphorase used is not particularly limited with the proviso that it is within a range for sufficiently effecting the reaction, but when cost, production and the like are taken into consideration, the range of its practical using amount is from 0.001 to 10,000 units, more preferably from 0.01 to 1,000 units, most suitably from 0.1 to 100 units, based on 1 ml of the reaction solution at the time of the reaction.

The chromogen to be used in the invention is a substance which develops a color of visualizable color tone, namely which generates a color having a light absorption within a partial or entire wavelength range of from 300 nm to 800 nm. This chromogen may be changed from a state having no absorption in the visible region into a state of having it, or from a state having the absorption region into a state of not having it, or changed into a state having different absorption spectrum, by said reaction, and more illustratively, it is a substance which shows a color through its reduction by the action of diaphorase in the presence of NAD (or NADP). For example, though not limited to the following examples, 2,6-dichlorophenolindophenol (to be referred to as DCPIP hereinafter) [Chemical Abstract Registration No. 620-45-1], methylene blue [Chemical Abstract Registration No. 61-73-4], resazurin [Chemical Abstract Registration No. 62758-13-8] and the like pigments and tetrazolium compounds are used.

Among them, tetrazolium compounds are particularly desirable, and their illustrative examples include p-iodonitrotetrazolium violet [Chemical Abstract Registration No. 146-68-9], MTT [Chemical Abstract Registration No. 298-93-1], neotetrazolium [Chemical Abstract Registration No. 298-95-3], nitro blue tetrazolium [Chemical Abstract Registration No. 298-83-9], tetranitro blue tetrazolium [Chemical Abstract Registration No. 42798-98-1], tetrazolium blue [Chemical Abstract Registration No.1871-22-3], tetrazolium red (triphenyl tetrazolium) [Chemical Abstract Registration No. 298-96-4], tetrazolium violet [Chemical Abstract Registration No.1719-71-7], thiocarbamyl nitro blue tetrazolium [Chemical Abstract Registration No. 36889-43-7], XTT [Chemical Abstract Registration No. 111072-31-2], WST-1 [Chemical Abstract Registration No.150849-52-8], WST-3 [Chemical Abstract unregistered] and the like or their salts and the like.

In addition, development of multiple colors can be effected by simultaneously using two or more tetrazolium compounds as the chromogen. This is a combination of similar reactions of conventional techniques (Japanese Patent No. 1,782,359, JP-A-62-239054 and the like), but since coupled reaction of enzymes in the coloration-inducing reaction is not taken into consideration in these conventional techniques, in spite of the broad coloration range, only one chromogen molecule is changed into its corresponding pigment based on one molecule of the substance to be measured so that measurable concentration range of the substance to be measured is limited to the concentration of substance to be measured contained in the measuring reagent solution. Since the concentration range of substance to be measured has a limitation in the measuring reagent solution, this broad coloration range was not able to be used effectively.

In the invention to which a coupled system of enzymes is applied, a substance to be measured is amplified by the enzyme reaction, so that increase in the apparent concentration of the substance to be measured can be optionally controlled by limiting optional reaction time, regardless the initial concentration of the substance to be measured. By applying this multiple color developing technique to the invention, it became possible to reflect the markedly broad concentration range of substance to be measured in response to the intention. This could not be accomplished by merely applying the conventional techniques but was accomplished for the first time by limiting concentration ratio and the like of chromogen in order to coincide necessary measuring concentration range with the coloration range, so that this cannot simply be deduced from the conventional techniques.

One example of the tetrazolium salts to be used for broadening the coloration range is DCPIP and the other is p-iodonitrotetrazolium violet, tetrazolium red, tetrazolium violet or the like. DCPIP is a pigment blue-colored by nature, which is a pigment having a property to become colorless and transparent by undergoing reduction by the action of diaphorase, an electron carrier or the like. Contrary to this, p-iodonitrotetrazolium violet, tetrazolium red, tetrazolium violet or the like is a pigment originally colorless or colored slightly yellow, which is a pigment having a property to show red to reddish purple color by undergoing reduction by the action of diaphorase, an electron carrier or the like. When DCPIP and p-iodonitrotetrazolium violet, tetrazolium red, tetrazolium violet or the like are simultaneously used, the solution initially colored blue becomes red to reddish purple via a short transparent period as the reducing reaction by the action of diaphorase, an electron carrier or the like progresses. By simultaneously using them, coloration from blue to red can be realized. Also, in addition to this, when the original solution is colored yellow using a pigment which hardly undergoes oxidation reduction, the originally colored yellow is observed during the transparent period of the aforementioned reaction, so that a coloration reaction changing from blue to red via yellow can also be realized in appearance by the reaction.

The amount of chromogen used is not particularly limited with the proviso that it is within a range for sufficiently effecting the reaction, but when cost, production and the like are taken into consideration, the range of its practical using amount is from 0.1 nanomol to 1,000 micromol, more preferably from 1 nanomol to 100 micromol, based on 1 ml of the reaction solution at the time of the reaction.

In addition, though the yellow pigment to be used in the coloring of the solution is not particularly limited with the proviso that the coloration of interest can be obtained and it does not inhibit the reaction, the diaphorase itself which is originally colored yellow, titanium yellow, food dye Yellow No. 3, food dye Yellow No. 4 or the like is used. It is preferably from 0.0001% to 1% in the reaction solution.

Concentration of the yellow pigment to be used herein is not particularly limited with the proviso that it is a concentration by which the coloration of interest can be confirmed. The coloration of interest can be attained by a markedly trace amount particularly when the pigment is used.

When the measuring method of the invention is carried out, it can be carried out by the following operations.

Since ATP is contained mostly in cells of organisms, the samples to be used in the invention may be organisms themselves or samples containing parts thereof which are generally used in a liquid state. However, materials which are dry in appearance such as powder can also be used as samples in some cases. When they are dry in appearance, these may be mixed directly with the reagent solution (plural or single) or mixed with other liquid to make into a dissolved state and then mixed with the reagent solution (plural or single).

In addition, since ATP is contained mostly in cells, in order to improve extraction efficiency of this ATP into sample solutions, the cells may be disrupted in advance using a surface active agent or an organic solvent.

When the measuring method of the invention is carried out in a dissolved state, it comprises a first step in which a sample containing ATP is mixed with a reagent solution containing at least acetyl phosphate, glucose, acetate kinase, glucokinase or hexokinase, nicotinamide adenine dinucleotide or nicotinamide adenine dinucleotide phosphate, a chromogen, glucose-6-phosphate dehydrogenase, and diaphorase or an electron carrier, a second step in which a pigment is formed at a rate responding to the amount of ATP and a third step in which the amount of ATP is calculated by determining the thus formed pigment.

The first step is a step for allowing at least ATP and acetyl phosphate, glucose, acetate kinase, glucokinase or hexokinase, nicotinamide adenine dinucleotide or nicotinamide adenine dinucleotide phosphate, a chromogen, glucose-6-phosphate dehydrogenase, and diaphorase or an electron carrier to be present in the same solution until reaching the second step, and when acetyl phosphate, glucose, acetate kinase, glucokinase or hexokinase, nicotinamide adenine dinucleotide or nicotinamide adenine dinucleotide phosphate, a chromogen, glucose-6-phosphate dehydrogenase, and diaphorase or an electron carrier are present in the same reagent solution, this is a step which includes one operation for mixing this reagent solution with a sample solution containing ATP, or when acetyl phosphate, glucose, acetate kinase, glucokinase or hexokinase, nicotinamide adenine dinucleotide or nicotinamide adenine dinucleotide phosphate, a chromogen, glucose-6-phosphate dehydrogenase, and diaphorase or an electron carrier are separately present in two or more reagent solutions, this is a step which includes operations necessary for mixing all of these solutions with a sample solution containing ATP wherein the number of operations increases in response to the number of the reagent solutions. That is, for example, when acetyl phosphate, glucose, acetate kinase, glucokinase or hexokinase, nicotinamide adenine dinucleotide or nicotinamide adenine dinucleotide phosphate, a chromogen, glucose-6-phosphate dehydrogenase and diaphorase or an electron carrier are separately present in two reagent solutions, it includes a first operation for mixing a sample solution with a first reagent solution and a subsequent second operation for mixing with a second reagent solution, or includes a first operation for preparing a new reagent solution by mixing the first reagent solution with the second reagent solution and a second operation for mixing this new reagent solution with a sample solution, or includes one operation for mixing these solutions at the same time. In addition, when some of these solutions are present under dried condition, this is a step which includes an additional operation for making them into a solution by the dropwise addition of a sample solution, a reagent solution or other certain liquid component thereto.

The second step is a step which is automatically generated in the solution after mixing of the sample solution with the reagent solution (single or plural). For effecting this step, it is necessary that pH of the mixed solution is at least within the range of from 2 to 12 and temperature of the mixed solution is within the range of from 10° C. to 80° C. In order to realize this, it is necessary to contain a buffer solution at least in a reagent solution, and though generally there are no problems when present under an environment where a human can act, an operation for maintaining or heating the mixed solution within said temperature range may be included for the purpose of positively keeping the temperature of the mixed solution within said range.

The third step includes an operation for determining a pigment formed at a rate responding to the amount of ATP as a first operation. When the mixed solution is contained in a test tube or the like, the determination of pigment includes an operation for measuring the amount of the pigment by measuring absorbance at a wavelength of from 300 to 800 nm, preferably from 400 to 800 nm, more preferably from 450 to 700 nm, using a spectrophotometer, or includes an operation for measuring it by comparing with the color for reference for determination. Also, when a small amount of a solution or gelatin containing necessary reagents is carried on a filter paper or the like support, and a pigment is formed under a condition of not a liquid in appearance, it includes an operation for measuring it by comparing with the color for reference for determination. In addition, the measurement of ATP from the amount of measured pigment includes a second operation for measuring the amount of ATP using a converting formula or the like prepared on each occasion or in advance.

Since changes in color tone periodically occur in response to the reaction time, a reaction terminator can be added to the reaction solution after a predetermined period of time or in advance, in order to terminate the reaction at an optional period of time and thereby to make a broad range of coloration more practical. As the reaction terminator, acetic anhydride, maleic anhydride, phthalic acid, sodium azide, iodine and the like generally known chemical enzyme modifiers can be firstly exemplified. When these chemical enzyme modifiers are allowed to coexist in the reaction solution, chemical modification of enzymes completes during their coupled reaction so that the enzymes are inactivated and the reaction is terminated after a predetermined period of time. It is known in general that chemical modifiers inhibit reactions by inactivating enzymes. It has been considered that when a chemical modifier is allowed to coexist in the reaction solution, the reaction does not progress due to inactivation of enzymes by first undergoing inhibition. This time, it was discovered that this inactivation of enzymes by chemical modification requires a more prolonged period of time than expected. It was found thereby that when an enzyme is allowed to exist with a chemical modifier, the main reaction progresses until the enzyme is inactivated, but the reaction is terminated after a certain period of time due to inactivation of the enzyme by the completion of its chemical modification. By applying this discovery, a reaction reagent was accomplished in which the main reaction progresses for a certain period of time and then the reaction is terminated due to inactivation of the enzyme, when the enzyme is allowed to coexist with a chemical modifier.

The kinds of chemical modifier to be used for this are not particularly limited with the proviso that the modification reaction of interest can be carried out. Its concentration is not particularly limited too, with the proviso that the modification reaction of interest can be carried out, but is respectively from 0.001% to 10%, preferably from 0.002% to 1%, more preferably from 0.01% to 0.5%, based on the reaction solution.

Separately from this, acetyl phosphate degradation accelerating agents can be exemplified as the reaction terminator. It was found that degradation of acetyl phosphate is accelerated when acetyl phosphate is allowed to coexist with zinc, iron, copper, magnesium, manganese and the like mainly divalent metal ions.

It was found thereby that when an acetyl phosphate degradation accelerator is allowed to coexist in a reaction system containing acetyl phosphate and the like, acetyl phosphate is gradually degraded by the acetyl phosphate degradation accelerator and the reaction is terminated after a certain period of time due to disappearance of acetyl phosphate. By applying this discovery, a reaction reagent was accomplished in which the main reaction progresses for a certain period of time and then the reaction is terminated due to disappearance of acetyl phosphate, when acetyl phosphate is allowed to coexist with an acetyl phosphate degradation accelerator.

The kinds of divalent metal ion are not particularly limited with the proviso that the degradation reaction of interest can be carried out, but zinc, manganese, iron and copper are preferably used. Its concentration is not particularly limited too, with the proviso that the termination reaction of interest can be carried out, but is a concentration of from 0.001 mmol to 10 mol, preferably from 0.01 mmol to 1 mol, more preferably from 0.1 mmol to 500 mmol, based on 1 liter of the reaction solution.

These acetyl phosphate degradation accelerators sufficiently attain the purpose when only one of them is allowed to coexist in the reaction solution, but there will be no problem when two or more of them are allowed to coexist. Also, an acetyl phosphate degradation accelerator and a chemical modifier may be jointly used as the reaction terminator.

In addition, it is desirable that the chromogen and reaction terminator exemplified herein are preferably present together with acetyl phosphate, glucose, NAD or NADH, acetate kinase, glucokinase (or hexokinase), glucose-6-phosphate dehydrogenase, diaphorase and ATP in the same solution at the same time at the time of the reaction, and their conditions are not particularly limited until the reaction and they may be in a liquid state, a powder state, a state impregnated into a test paper, nonwoven fabric or the like, or even a state dried on a test paper or nonwoven fabric, each independently, at the same time or as a combination of two or more.

EXAMPLES

The following illustratively describes the invention based on examples.

A spectrophotometer U-3210 manufactured by Hitachi was used for the measurement of reactions. Regarding the color for reference for visual determination, the 5PB- V3N10, V5N8, V7N4, V9N2 and white shown on page 30 of the JIS Z8721-based standard color gloss plates published by Japanese Standards Association were respectively used as determination strengths +4, +3, +2, +1 and 0, by referring to the spectrophotometer results. Acetate kinase (*Bacillus stearothezmophilus* origin), glucokinase (*Bacillus stearothermophilus* origin) and diaphorase (diaphorase I of *Bacillus stearothermophilus* origin) manufactured by UNITIKA were purchased and used. Also, hexokinase (yeast origin) and glucose-6-phosphate dehydrogenase (*Leuconostoc mesenteroides* origin) manufactured by Roche were purchased and used. Regarding the units of respective enzymes, the indicated units described on the labels at the time of their purchase were used as such.

Example 1

Figure 2:
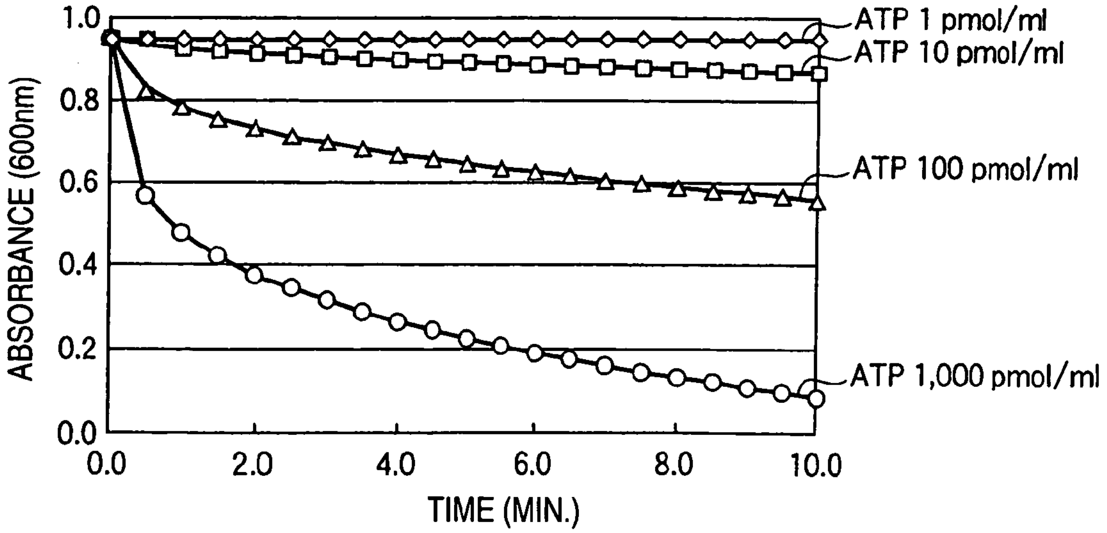
FIG. 2 is a graph showing periodical changes in the absorbance when ATP of varied concentration was measured by the ATP measuring reagent of the invention using DCPIP as the chromogen.
Figure 3:
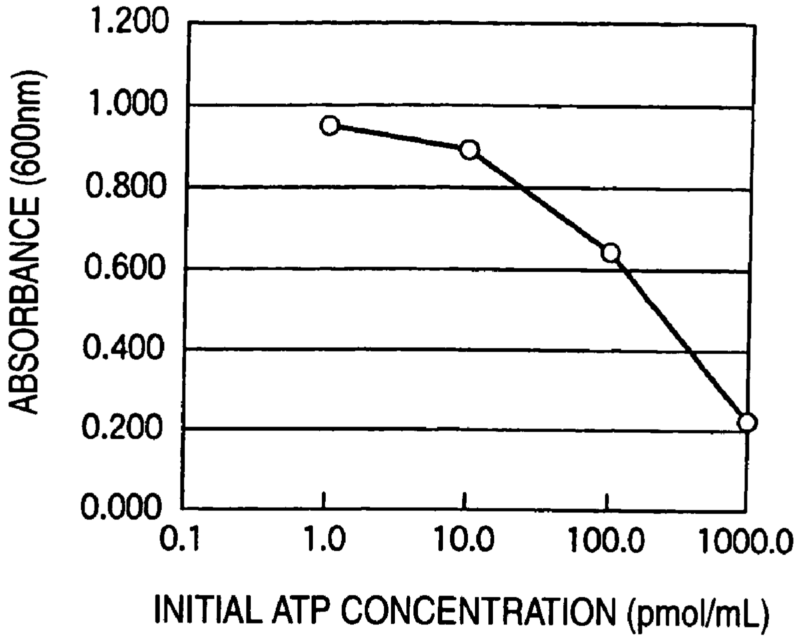
FIG. 3 is a graph showing a calibration curve when ATP of varied concentration was measured by the ATP measuring reagent of the invention using DCPIP as the chromogen.

A 2.7 ml portion of 50 mmol in concentration of Tris-HCl buffer (pH 7.5) containing 10 mmol of acetyl phosphate, 10 mmol of glucose, 1 mmol of NAD and 50 pmol of DCPIP and 0.3 ml of 50 mmol in concentration of Tris-HCl buffer (pH 8.0) containing 10 units of acetate kinase, 10 units of hexokinase, 10 units of glucose-6-phosphate dehydrogenase and 10 units of diaphorase, each per ml, were added dropwise to a spectrophotometer standard cell kept at 37° C., and 0.1 ml of a sample solution containing ATP was added thereto and thoroughly stirred. Changes in the absorbance at 600 nm were measured by the spectrophotometer. The results are shown in FIG. 2. Also, values of the absorbance measured by the spectrophotometer 5 minutes after the reaction were plotted against respective ATP initial concentrations, with the results shown in FIG. 3. Based on these results, it was found that ATP can be properly measured when DCPIP is used as the chromogen.

Example 2

Figure 4:
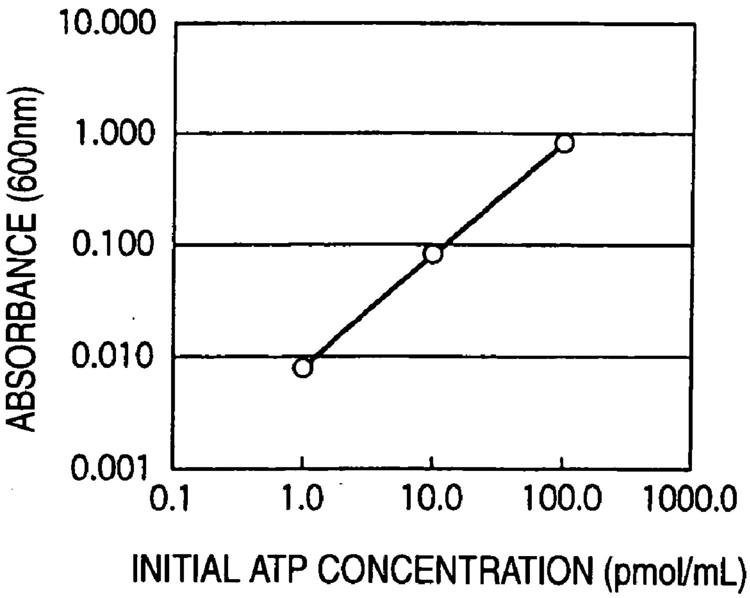
FIG. 4 is a graph showing a calibration curve when ATP of varied concentration was measured by the ATP measuring reagent of the invention using tetrazolium as the chromogen.

A 2.7 ml portion of 25 mmol in concentration of sodium phosphate buffer (pH 7.0) containing 5 mmol of acetyl phosphate, 5 mmol of glucose, 1 mmol of NAD and 1 mmol of tetrazolium blue, and 10 μl for each of 10 mmol in concentration of sodium phosphate buffer (pH 7.0) containing 100 units of acetate kinase, 10 mmol in concentration of sodium phosphate buffer (pH 7.0) containing 1,000 units of hexokinase, 10 mmol in concentration of sodium phosphate buffer (pH 7.0) containing 1,000 units of glucose-6-phosphate dehydrogenase and 10 mmol in concentration of sodium phosphate buffer (pH 7.0) containing 1,000 units of diaphorase, each per ml, were added dropwise to a spectrophotometer standard cell kept at 37° C., and 50 μl of a sample solution containing ATP was added thereto and thoroughly stirred. The absorbance at 600 nm was measured by the spectrophotometer 5 minutes thereafter. The results are shown in FIG. 4. As a result, it was found that ATP can be properly measured when tetrazolium blue is used as the chromogen.

Example 3

A 4.5 ml portion of 50 mmol in concentration of Tris-HCl buffer (pH 7.5) containing 10 mmol of acetyl phosphate, 10 mmol of glucose, 1 mmol of NAD and 50 μmol of DCPIP and 0.5 ml of 50 mmol in concentration of Tris-HCl buffer (pH 8.0) containing 1 unit of acetate kinase, 1 unit of hexokinase, 1 unit of glucose-6-phosphate dehydrogenase and 1 unit of diaphorase, each per ml, were added dropwise to a 15 ml capacity test tube and mixed. A 1.0 ml portion of a sample solution containing ATP to a final ATP concentration of 0, 1, 10, 100, 1,000 or 10,000 pmol per ml reaction reagent was added thereto, and the mixture was thoroughly stirred and allowed to stand at room temperature for 10 minutes. Thereafter, intensity of color was judged using a color for reference for judgment.

The results are shown in Table 1. Since the reagent is colored blue originally, it is blue and the color intensity becomes +4 when ATP is not present in the reaction solution. Also, when ATP is present in a large amount exceeding measuring limit of the reagent, blue color of the reagent completely disappears and the reaction solution becomes transparent with a color intensity of 0. Based on the result, approximate concentration of the initial concentration of ATP was able to be judged within the range of the ATP final concentration of from 1 pmol to 10,000 pmol per mol reaction reagent.

TABLE 1

| | ATP initial concentration (pmol/ml) | | | | | |
|---|---|---|---|---|---|---|
| | 0 | 1 | 10 | 100 | 1000 | 10000 |
| Judgment | +4 | +4 | +3 | +2 | +1 | 0 |

Example 4

A 4.5 ml portion of 50 mmol in concentration of Tris-HCl buffer (pH 7.5) containing 10 mmol of acetyl phosphate, 10 mmol of glucose, 1 mmol of NAD, 10 μmol of DCPIP, 0.1% of p-nitroiodotetrazolium violet and 0.02% of Yellow No. 3, and 0.5 ml of 50 mmol in concentration of Tris-HCl buffer (pH 8.0) containing 1 unit of acetate kinase, 1 unit of hexokinase, 1 unit of glucose-6-phosphate dehydrogenase and 5 units of diaphorase, each per ml, were added dropwise to a 15 ml capacity test tube and mixed. A 1.0 ml portion of a sample solution containing ATP to a final ATP concentration of 0, 1, 10, 100, 1,000 or 10,000 pmol per ml reaction reagent was added thereto, and the mixture was thoroughly stirred and allowed to stand at room temperature for 30 minutes. Thereafter, the color was judged with the naked eye.

The results are shown in Table 2. Based on these results, approximate concentration of the initial concentration of ATP was able to be judged within the range of the ATP final concentration of from 1 pmol to 1,000 pmol per mol reaction reagent.

TABLE 2

| | Visual judgment of ATP by multiple color development | | | | |
|---|---|---|---|---|---|
| | ATP initial concentration (pmol/ml) | | | | |
| | 0 | 1 | 10 | 100 | 1000 |
| Judgment | Blue | Green | Yellow | Orange | Red |

Example 5

Figure 5:
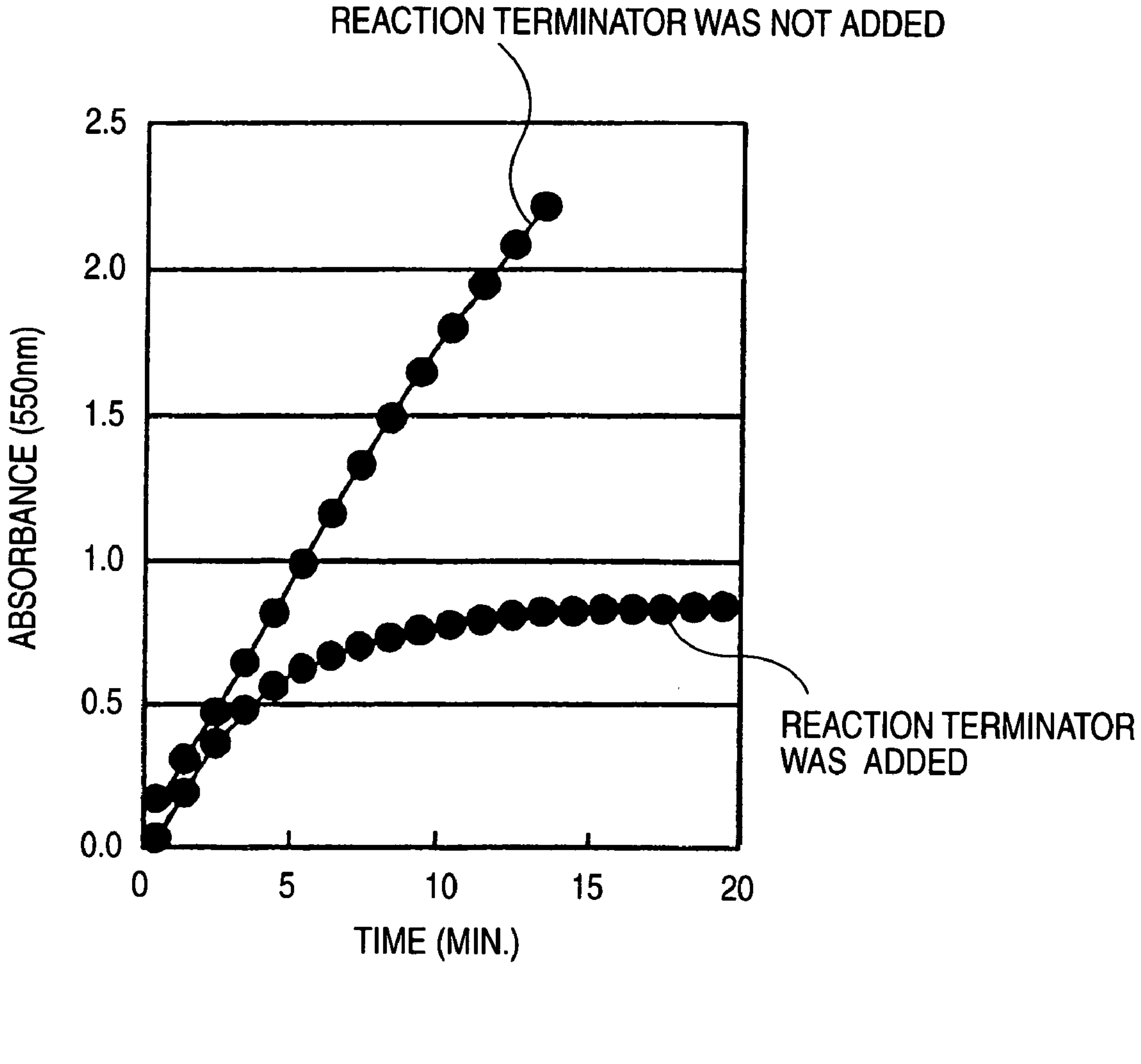
FIG. 5 is a graph showing a comparison of a reaction curve in the case of not adding a reaction terminator (chemical modifier) with a reaction curve in the case of adding a reaction terminator (chemical modifier).

A 1.0 ml portion of a sample solution containing ATP to a final ATP concentration of 100 pmol per ml reaction reagent was added to and thoroughly mixed with 4.5 ml of 50 mmol in concentration of Tris-HCl buffer (pH 7.5) containing 10 mmol of acetyl phosphate, 10 mmol of glucose, 1 mmol of NAD, 0.1% of tetrazolium violet and 0.1% of phthalic acid as a chemical modifier, to which was added dropwise 0.5 ml of 50 mmol in concentration of Tris-HCl buffer (pH 8.0) containing 1 unit of acetate kinase, 1 unit of hexokinase, 1 unit of glucose-6-phosphate dehydrogenase and 5 units of diaphorase, each per ml, in a 15 ml capacity test tube and mixed. Under such a coexisting condition of enzymes, substrates and a chemical modifier, ATP-dependent coloring reaction was periodically monitored based on the changes in absorbance at 550 nm. The results are shown in FIG. 5. Other results measured by the same operation except that phthalic acid was not contained are also shown in FIG. 5.

It was found from the results of FIG. 5 that the reaction was terminated after about 20 minutes by the addition of phthalic acid.

Example 6

Figure 6:
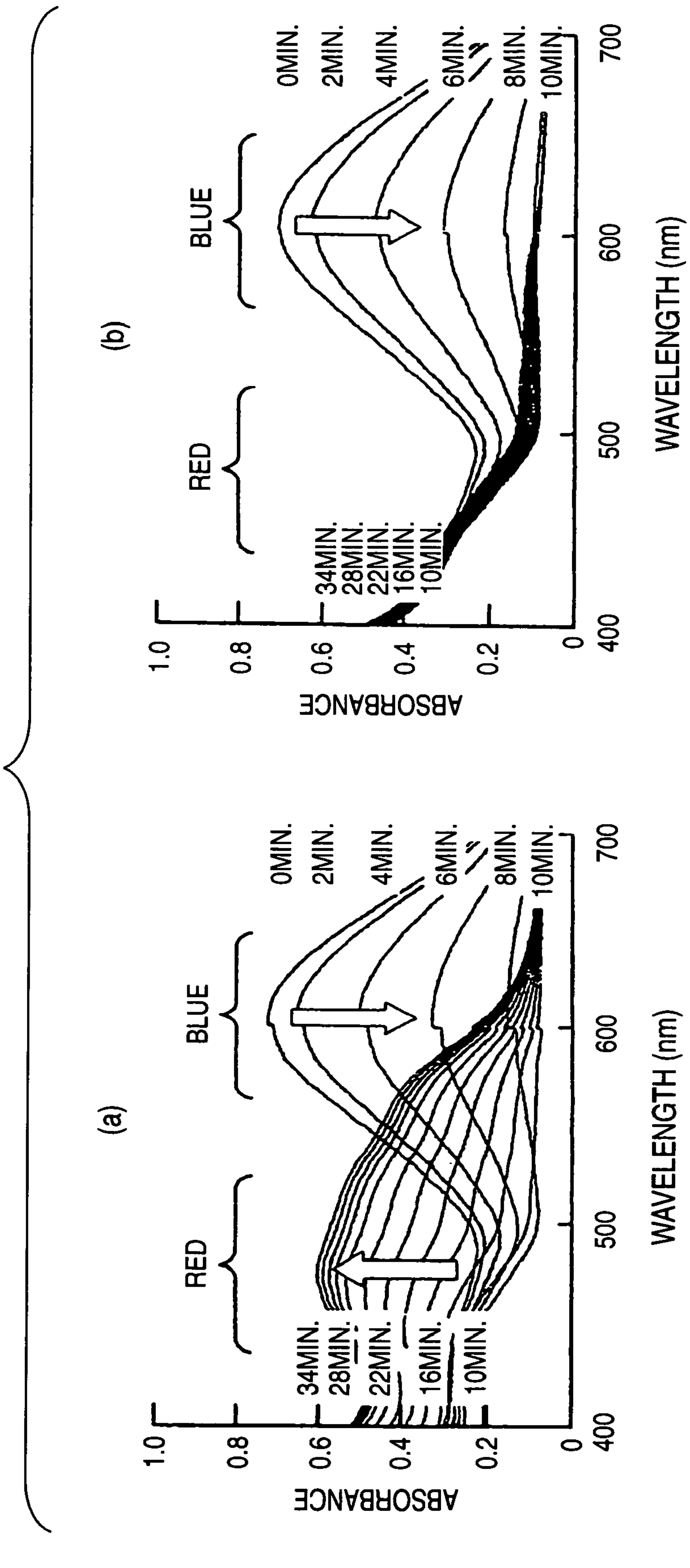
FIG. 6 is a graph showing a comparison of a case (a) in which a reaction terminator (an acetyl phosphate degradation accelerator) is not added to a multiple color developing system with a case (b) in which a reaction terminator (an acetyl phosphate degradation accelerator) is added.

A 4.5 ml portion of 50 mmol in concentration of Tris-HCl buffer (pH 7.5) containing 10 mmol of acetyl phosphate, 10 mmol of glucose, 1 mmol of NAD, 0.005% of DCPIP, 0.1% of p-nitroiodotetrazolium violet and 0.002% of Yellow No. 3, and 0.5 ml of 50 mmol in concentration of Tris-HCl buffer (pH 8.0) containing 1 unit of acetate kinase, 1 unit of hexokinase, 1 unit of glucose-6-phosphate dehydrogenase and 5 units of diaphorase, each per ml, and also containing 5 mmol in final concentration of iron ion as an acetyl phosphate degrading agent were added dropwise to a 15 ml capacity test tube and mixed. A 1.0 ml portion of a sample solution containing ATP to a final ATP concentration of 10 pmol per ml reaction reagent was added thereto and thoroughly stirred. Under such a condition of simultaneously containing an acetyl phosphate degradation accelerating agent, ATP-dependent coloring reaction was periodically monitored based on the changes in the absorbance at from 400 nm to 700 nm. The results are shown in FIG. 6. Also, changes in color during this period were judged with the naked eye. The results are shown in Table 3. Other results measured by the same operation except that iron ion was not contained are also shown in FIG. 6 and Table 3.

It was found from the results of FIG. 6 and Table 3 that the reaction was terminated after about 15 minutes by the addition of iron ion.

TABLE 3

Visual determination of ATP by multiple color development

| | Reaction time (min) | | | | | | |
|---|---|---|---|---|---|---|---|
| | 0 | 5 | 10 | 15 | 20 | 25 | 30 |
| Terminator added | Blue | Green | Yellow | Yellow | Yellow | Yellow | Yellow |
| Terminator not added | Blue | Green | Yellow | Orange | Orange | Red | Red |

Thus, based on the results shown in Examples 1 to 6, it was found that ATP can be measured satisfactorily by the measuring method described in the invention. Also, it was found that an approximate concentration of ATP can be determined by visual observation. In addition, it became possible to terminate the reaction after a practically sufficient period of time.

While the invention has been described in detail and with reference to specific embodiments thereof, it will be apparent to one skilled in the art that various changes and modifications can be made therein without departing from the spirit and scope of the invention.

This application is based on Japanese patent application filed on Nov. 21, 2001 (Japanese Patent Application No. 2001-356141), the entire contents thereof being hereby incorporated by reference.

INDUSTRIAL APPLICABILITY

The invention has rendered possible provision of a visually determinable ATP measuring reagent which can be easily handled and has good measuring sensitivity.

The invention claimed is:

1. A method for visually measuring a level of ATP in a sample comprising:

i) forming glucose-6-phosphate in the presence of the ATP in the sample with, acetyl phosphate and glucose, and by a reaction of a coupled enzyme reaction system comprising an acetate kinase enzyme and one of a glucokinase enzyme or a hexokinase enzyme;

ii) changing a color state of a chromogen subsequently in response to the amount of formed glucose 6-phosphate, by a reaction of another coupled enzyme reaction system comprising:

a glucose-6-phosphate dehydrogenase enzyme and a diaphorase enzyme; or a glucose-6-phosphate dehydrogenase enzyme and an electron carrier, in the presence of nicotinamide adenine dinucleotide or nicotinamide adenine dinucleotide phosphate and in the presence of a chromogen, and iii) determining the level of ATP in the sample by measuring the change in the color state of said chromogen.

2. The method for visually measuring the level of ATP in a sample of claim 1, wherein said chromogen is a dichlorophenolindophenol and a tetrazolium or a salt thereof and one of said coupled enzyme reaction system or said another coupled enzyme reaction system contains a pigment for coloring.

3. The method for visually measuring the level of ATP in a sample of claim 1 or claim 2, wherein at the reaction of least one of said coupled enzyme reaction systems is terminated by at least one of a chemical enzyme modifier and an acetyl phosphate degradation accelerator.

4. The method for visually measuring the level of ATP in a sample of claim 1, wherein 6-phosphogluconolactonase is present in the sample.

5. The method for visually measuring the level of ATP in a sample of claim 1, wherein 6-phosphogluconate dehydrogenase is present in the sample.

6. The method for visually measuring the level of ATP in a sample of claim 1, wherein an acetyl phosphate degradation accelerating agents is present in the sample.

7. The method for visually measuring the level of ATP in a sample of claim 1, wherein a divalent metal ion is present in the sample.

8. A reagent for visually measuring a level of ATP in a sample, comprising:

acetyl phosphate;

glucose;

an acetate kinase enzyme;

one of a glucokinase enzyme or a hexokinase enzyme, a chromogen;

nicotinamide adenine dinucleotide or nicotinamide adenine dinucleotide phosphate; and a glucose-6-phosphate dehydrogenase enzyme and a diaphorase enzyme, or a glucose-6-phosphate dehydrogenase enzyme and an electron carrier, said reagent which forms glucose 6-phosphate in response to the ATP in the sample and changing the color state of the chromogen in response to the amount of formed glucose 6-phosphate.

9. The reagent for visually measuring the level of ATP in a sample of claim 8, wherein further comprising a pigment for coloring and said chromogen is a dichlorophenolindophenol and a tetrazolium or a salt thereof.

10. The reagent of claim 8 or claim 9, wherein said reagent further comprises at least one member selected from the group consisting of a chemical enzyme modifier and an acetyl phosphate degradation accelerator.

11. The reagent for visually measuring the level of ATP in a sample of claim 8, wherein said reagent is capable of determining ATP concentration in a range of 1 pmole to 10,000 pmole per mole of said reagent.

12. The reagent for visually measuring the level of ATP in a sample of claim 11, wherein said reagent determines ATP concentration in a range of 1 pmole to 1,000 pmole per mole of said reagent.

13. The method for visually measuring the level of ATP in a sample of claim 1, wherein said change in the color state of said chromogen is a change from a state having no absorption in the visible region into a state of having absorption in the visible region, a change from a state having absorption in the visible region into a state of not having absorption in the visible region, or a change into a state having different absorption spectrum.

14. The method for visually measuring the level of ATP in a sample of claim 13, wherein said wherein said change in the color state of said chromogen is measured by a spectrophotometer.

15. The method for visually measuring the level of ATP in a sample of claim 14, wherein said wherein said change in the color state of said chromogen is measured by measuring absorbance at a wavelength in the range of from 300 to 800 nm.

16. The method for visually measuring the level of ATP in a sample of claim 14, wherein said wherein said change in the color state of said chromogen is measured by measuring absorbance at a wavelength in the range of from 400 to 800.

17. The method for visually measuring the level of ATP in a sample of claim 14, wherein said wherein said change in the color state of said chromogen is measured by measuring absorbance at a wavelength in the range of from 450 to 700 nm.

* * * * *